(12) United States Patent
Törnblom (10) Patent No.: US 9,764,126 B2
(45) Date of Patent: Sep. 19, 2017

(54) VALVE FOR ADMINISTRATION OF A PLURALITY OF DRUG FLUIDS

(75) Inventor: Micael Törnblom, Helsingborg (SE)

(73) Assignee: CYTO365 AB, Helsingborg (SE)

( * ) Notice: Subject to any disclaimer, the term of this patent is extended or adjusted under 35 U.S.C. 154(b) by 205 days.

(21) Appl. No.: 14/350,041

(22) PCT Filed: Jun. 12, 2012

(86) PCT No.: PCT/SE2012/050630
§ 371 (c)(1),
(2), (4) Date: Jul. 21, 2014

(87) PCT Pub. No.: WO2013/055278
PCT Pub. Date: Apr. 18, 2013

(65) Prior Publication Data
US 2014/0346386 A1  Nov. 27, 2014

(30) Foreign Application Priority Data
Oct. 10, 2011  (SE) ...................................... 1150932

(51) Int. Cl.
*A61M 39/22* (2006.01)
*F16K 11/076* (2006.01)
*F16K 11/085* (2006.01)

(52) U.S. Cl.
CPC ......... *A61M 39/223* (2013.01); *F16K 11/076* (2013.01); *F16K 11/0856* (2013.01); *Y10T 137/86566* (2015.04)

(58) Field of Classification Search
CPC  A61M 39/223; F15K 11/0856; F16K 11/076; Y10T 137/86566
(Continued)

(56) References Cited

U.S. PATENT DOCUMENTS 1,469,612 A  *  10/1923  Bahr ..................... F16K 11/085
                                                                137/625.17
2,485,842 A       10/1949  Pennington
(Continued)

FOREIGN PATENT DOCUMENTS

DE        35 03 044 A1     7/1986
WO        91/18632 A1     12/1991
(Continued)

OTHER PUBLICATIONS

International Search Report and Written Opinion mailed Sep. 5, 2012, issued in corresponding International Application No. PCT/SE2012/050630, filed Jun. 12, 2012, 8 pages.
(Continued)

*Primary Examiner* — Jessica Cahill
*Assistant Examiner* — Daphne M Barry
(74) *Attorney, Agent, or Firm* — Christensen O'Connor Johnson Kindness PLLC (57) ABSTRACT

In accordance with the present inventive concept, there is provided a valve for administration of a plurality of drug fluids, such as cytostatics. The valve comprises: a housing having a plurality of circumferentially distributed primary inlets for receiving a respective one of the drug fluids and a secondary inlet for receiving a secondary fluid, such as a neutral fluid, an outlet, and a valve member arranged in the housing. The housing has a plurality of primary valve positions in each of which an associated one of the primary inlets is connected to the outlet, and a plurality of intermediary valve positions in each of which the secondary inlet is connected to the outlet. Moreover, the valve member has a outer surface sealingly engaging an inner surface of the housing, such that the primary and secondary inlets are sealingly connected to openings arranged in the outer surface of the valve member in each of the primary and
(Continued)

intermediary valve positions, respectively. Figure for publication.

8 Claims, 7 Drawing Sheets

(58) Field of Classification Search
USPC .......................................................... 137/602
See application file for complete search history.

(56) References Cited

U.S. PATENT DOCUMENTS

| | | | |
|---|---|---|---|
| 3,618,637 A | 11/1971 | Santomieri | |
| 3,834,372 A | 9/1974 | Turney | |
| 3,957,082 A | 5/1976 | Fuson | |
| 4,219,021 A | 8/1980 | Fink | |
| 4,604,093 A * | 8/1986 | Brown | A61M 5/16827 |
| | | | 137/625.11 |
| 4,608,996 A * | 9/1986 | Brown | A61B 5/0215 |
| | | | 600/348 |
| 4,758,235 A | 7/1988 | Tu | |
| 4,900,322 A | 2/1990 | Adams | |
| 4,967,797 A | 11/1990 | Manska | |
| 5,097,840 A * | 3/1992 | Wallace | A61B 5/021 |
| | | | 137/625.17 |
| 5,104,387 A | 4/1992 | Pokorney | |
| 5,135,026 A | 8/1992 | Manska | |
| 5,146,951 A * | 9/1992 | Chuang | E03C 1/0403 |
| | | | 137/594 |
| 5,288,290 A | 2/1994 | Brody | |
| 5,439,452 A | 8/1995 | McCarty | |
| 5,647,845 A | 7/1997 | Haber | |
| 7,984,730 B2 | 7/2011 | Ziv | |
| 8,478,385 B2 * | 7/2013 | Liu | A61B 6/481 |
| | | | 600/432 |
| 2006/0089603 A1 | 4/2006 | Truitt | |
| 2010/0305507 A1 | 12/2010 | Duncan | |
| 2011/0071390 A1 | 3/2011 | Liu | |
| 2014/0224829 A1 | 8/2014 | Capone | |

FOREIGN PATENT DOCUMENTS

| | | |
|---|---|---|
| WO | 2006/025054 A2 | 3/2006 |
| WO | 2011/011057 A2 | 1/2011 |
| WO | 2013/146752 A1 | 10/2013 |

OTHER PUBLICATIONS

International Search Report mailed Nov. 21, 2014, issued in corresponding International Application No. PCT/EP2014/069275, filed Sep. 10, 2014, 3 pages.

Extended European Search Report mailed Jun. 9, 2015, issued in corresponding European Application No. EP 12840058.7, filed Jun. 12, 2012, 6 pages.

* cited by examiner

VALVE FOR ADMINISTRATION OF A PLURALITY OF DRUG FLUIDS

FIELD OF THE INVENTION

The present inventive concept generally relates to administration of drug fluids. More specifically, the present inventive concept relates to valves for administration of drug fluids, such as cytostatics.

BACKGROUND OF THE INVENTION

There are plenty of medical situations in which a multiple of drug fluids to be inserted into a patient has to be handled. Typically, the various drug fluids are selected and branched by means of a drug-fluid valve. Moreover, in chemotherapy it is often of utmost importance to handle drug fluids to a patient which is treated for cancer in a reliable and safe manner. However, due to stressful working environments, tiredness, the human factor, etc., the handling of these drug fluids, including their connections, dosages, etc. often lead to errors. For example, the wrong type of drug fluid may be introduced into the wrong input site of the valve, which ultimately might damage the health of the patient. In addition, there is a need to clearly separate different fluids from each other, since they may chemically react in an undesired manner.

The disclosure U.S. Pat. No. 4,604,093 describes a valve for reliably administering multiple fluid infusions by means of a rotatable valve. In between infusions of drug fluids, a neutral solution is provided to the patient, thereby ensuring separation between the drug fluids.

However, there is need for a valve which is easy and cheap to manufacture.

SUMMARY OF THE INVENTION

It is therefore an object with the present inventive concept to provide a valve for administration of a plurality of drug fluids enabling fail safe use and which is easy and cheap to manufacture.

According to the inventive concept, there is provided a valve for administration of a plurality of drug fluids, such as cytostatics. The valve comprises a housing having a plurality of circumferentially distributed primary inlets for receiving a respective one of the drug fluids and a secondary inlet for receiving a secondary fluid, such as a neutral fluid, an outlet, and a valve member arranged in the housing. The housing has a plurality of primary valve positions in each of which an associated one of the primary inlets is connected to the outlet, and a plurality of intermediary valve positions in each of which the secondary inlet is connected to the outlet. The valve is characterized in that the valve member has a outer surface sealingly engaging an inner surface of the housing, such that the primary and secondary inlets are sealingly connected to openings arranged in the outer surface of the valve member in each of the primary and intermediary valve positions, respectively.

The inventive valve is preferably intended for one complete treatment use. Since the valve may be a disposable product which may be used in large quantities, it should preferably be easy and cheap to manufacture. Indeed, an advantage of the present inventive concept is that the housing and the valve member comprised in the valve may be manufactured by means of molding, such as injection molding. More specifically, the housing and the valve member may each be manufactured in a single piece. Consequently, the manufacturing and assembly of the valve becomes simpler and cheaper while keeping the fail safe characteristics of the valve.

An additional advantage of the present inventive concept is that there will be no residual aggregation of the secondary fluid within the valve while one of the plurality of drug fluids is being received in the valve. This is because of the sealed engagement of the valve member and the housing. An additional advantage of the sealed engagement, is that the risk of an unintentional mixing of fluids within the valve, for example due to a leakage, e.g. caused by broken parts within the valve, is reduced.

According to one embodiment, the housing is cylindrical, having a cylindrical inner surface, and the valve member is cylindrical, having a cylindrical outer surface According to one embodiment, the valve member is rotatably arranged in the housing. By means of being rotable, the valve member may be rotated into the primary valve positions as well as the intermediary valve positions, which thereby enables reliable selection operations for the different fluids.

According to one embodiment, the primary inlets are integrally formed with the housing. An advantage of this embodiment is that the primary inlets may be molded simultaneosly with the housing, e.g. by injection molding.

According to one embodiment, the openings comprise a first set of openings for the primary inlets and a second set of openings for the secondary inlet, the first set of openings being axially separated from the set of openings. An advantage of this embodiment is that the risk of unintentional mixing of fluids is reduced, since the first and second set of openings, and thereby also the primary inlets and the secondary inlet, are distinctly spatially separated from each other. Openings comprised in either one of said sets of openings may be mutually axially separated or may be arranged in a single plane.

According to one embodiment, the first set of openings comprises one opening. By means of this opening, the drug fluids may one at the time be led to the outlet via the valve member.

According to one embodiment, the second set of openings comprises at least one opening. By means of these openings, the secondary fluids may be led to the outlet via the valve member.

According to one embodiment, the second set of openings comprises at least a number of openings corresponding to the number of primary inlets.

According to one embodiment, the second set of openings comprises a number of openings corresponding to the number of primary inlets plus one.

Other features and advantages of embodiments of the present invention will become apparent to those skilled in the art upon review of the following drawings, the detailed description, and the appended claims.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings, where like reference numerals will be used for like elements, wherein:

FIG. 6b is cross-sectional side view taken along the line A-A in FIG. 6a.

DETAILED DESCRIPTION OF PREFERRED EMBODIMENTS

The present inventive concept relates to disposable valves for administration of a plurality of drug fluids. For example, the drug fluids may include various types of cytostatics which are to be infused into the vascular system of a patient intravenously in order to treat her/him from cancer. Other fluids which may be administered by the present inventive valve include volume expanders, blood-based products, blood substitutes, medications, nutritional solutions, etc.

The inventive concept ensures administration of a neutral fluid in connection with switching from one drug fluid to another. The drug fluids and the neutral fluid are preferably stored in bags on a rack at levels which are spatially higher than the entry into the vein of the patient, so that that these fluids may pass downwards by means of the gravitational force. Typically, the bags store 500 ml or 1000 ml of fluid. Alternatively, the fluids may be stored in vials or containers of similar types. According to another alternative, the fluids may be passed to the vein of the patient by means of a pump device. Moreover, the fluids are passed in tubes to a valve, which comprises a plurality of fluid inlets for the fluids. The valve will alternately distribute the drug fluids and the neutral fluid, as will be elaborated below. After passing the valve, one of the drug fluids or the neutral fluid is transported to a peripheral intravenous line arranged on the patient by means of a catheter tube. The fluid is thereafter led into the patient by means of a catheter which is placed into a peripheral vein.

In one example, a drip chamber is provided between the valve and the patient in order to prevent gas, such as air, from passing into the bloodstream of the patient, which might e.g. result in gas embolism.

In another example, a drip chamber may be provided before the valve. Preferably, one drip chamber is provided in connection to each bag storing the fluids.

In addition, a booster pump may be utilized in order to ensure that the drip chamber never becomes empty of fluid. The booster pump may maintain a predetermined pressure in the tube, and may thereby prevent gas from passing into the bloodstream of the patient. In one example, the booster pump is provided before the valve. In another example, the booster pump is provided after the valve.

Figure 1:
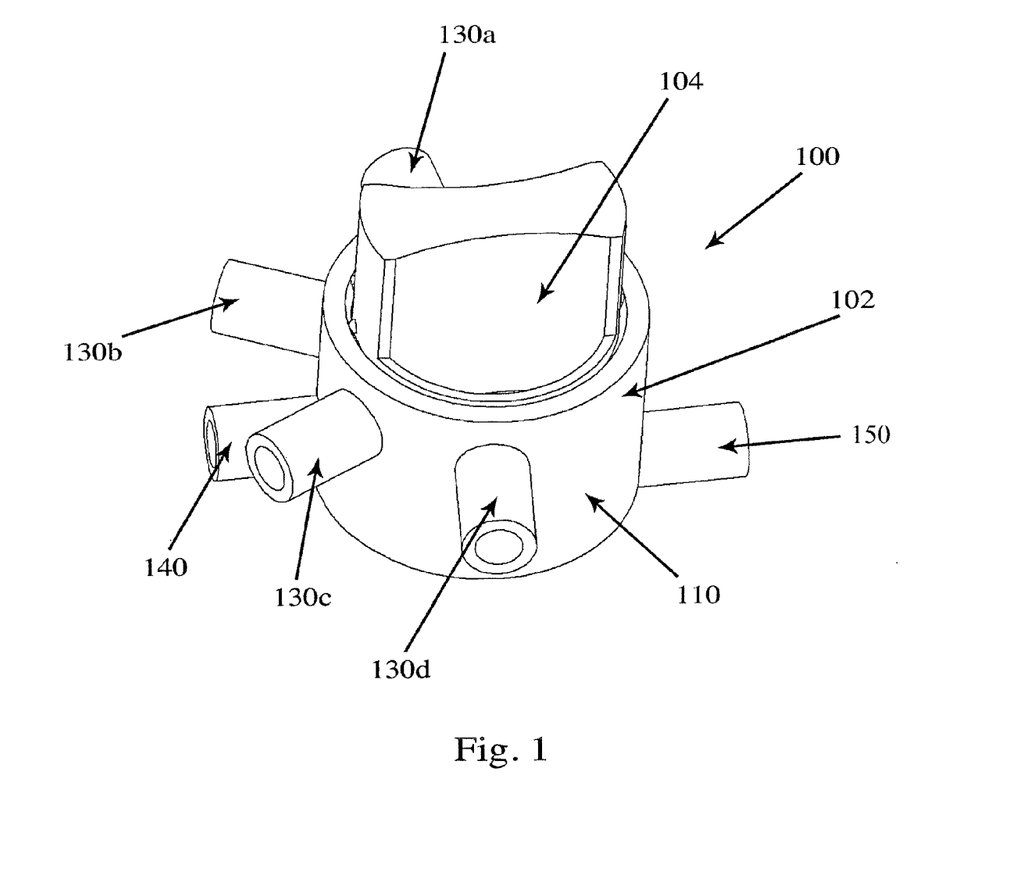
FIG. 1 is a perspective view of the valve as seen from the top side according to an embodiment of the present inventive concept.

Initially referring to FIG. 1, which is a perspective view of an embodiment of the valve as seen from the top side, the valve 100 for administration of a plurality of drug fluids comprises a cylindrical housing 102 and a cylindrical valve member 104 which is rotatably arranged in the housing 102. By cylindrical is here meant a cylinder-shape with constant radius. According to an alternative embodiment, the housing and the valve member have shapes other than cylindrical. For example, they may be frustoconical, comprised of several frustoconical parts, etc. More specifically, an outer cylindrical surface of the valve member 104 engages sealingly with an inner cylindrical surface 112 of the housing 102, thereby creating an assemblage which is airtight and prevents the flow of fluids. Preferably, the diameter of the outer cylindrical surface of the valve member 104 is slightly larger than the inner cylindrical surface of the housing 102 in order to create the sealed engagement mentioned above.

Alternatively, other ways of engaging sealingly is conceivable. In one example, a sealing element may be arranged in between the outer cylindrical surface of the valve member and the inner cylindrical surface of the housing. For example, the sealing element may be made of a thin, flexible material which may be fitted snugly between the valve member and the housing. For example, the sealing member may be an O-ring.

The housing 102 and the valve member 104 may be fabricated in any material which does not react chemically to any considerably extent with the intended drug fluids to be used, and which thereby and also in other aspects is suitable for medical applications. Moreover, the material must be suitable for sterile environments. Examples of materials include plastic materials. The plastic material may be transparent or opaque depending on the medical application.

The housing 102 may be fabricated in the same material as the valve member 104. Alternatively, the housing 102 may be fabricated in a material which is different from that of the valve member 104. In particular, the material of the housing 102 and the valve member may have different hardness.

Figure 2:
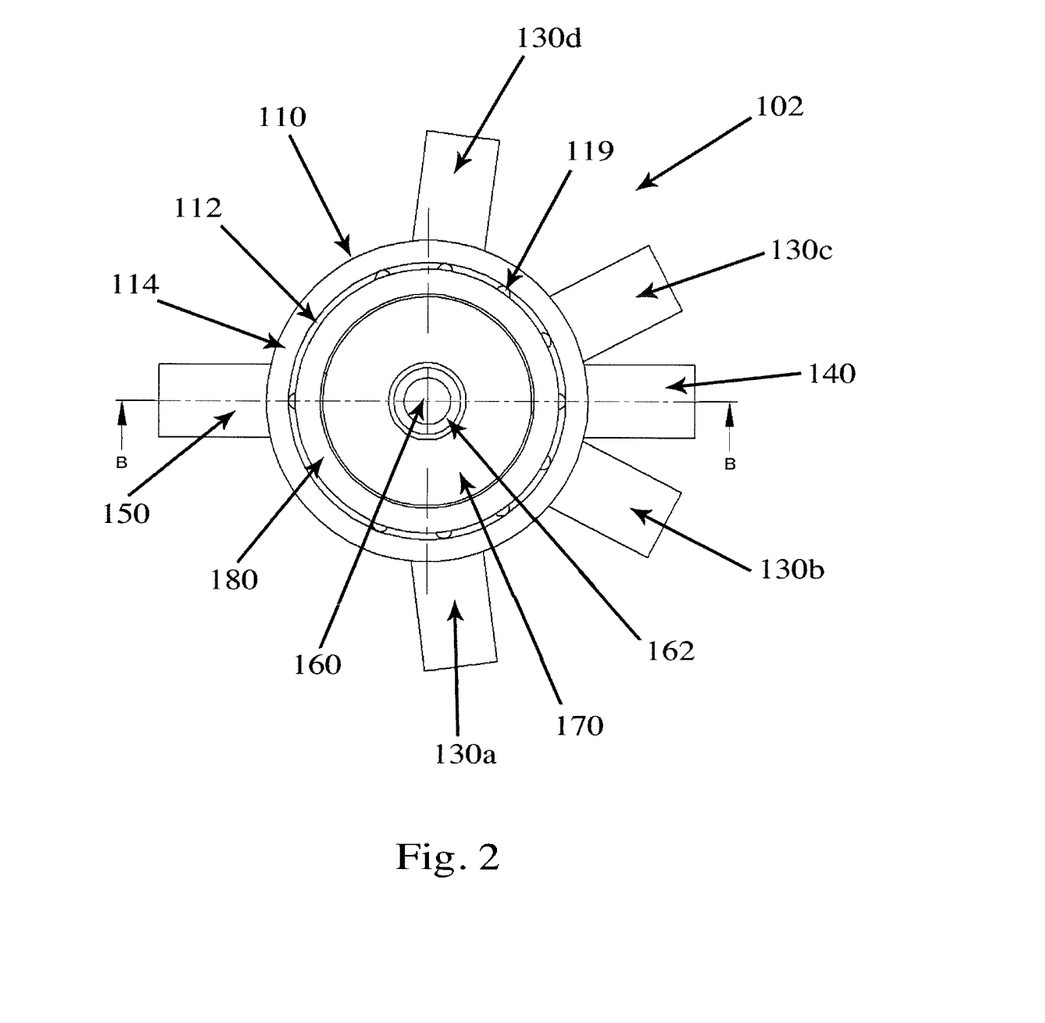
FIG. 2 is a top view of the cylindrical housing comprised in the valve shown in FIG. 1.
Figure 3A:
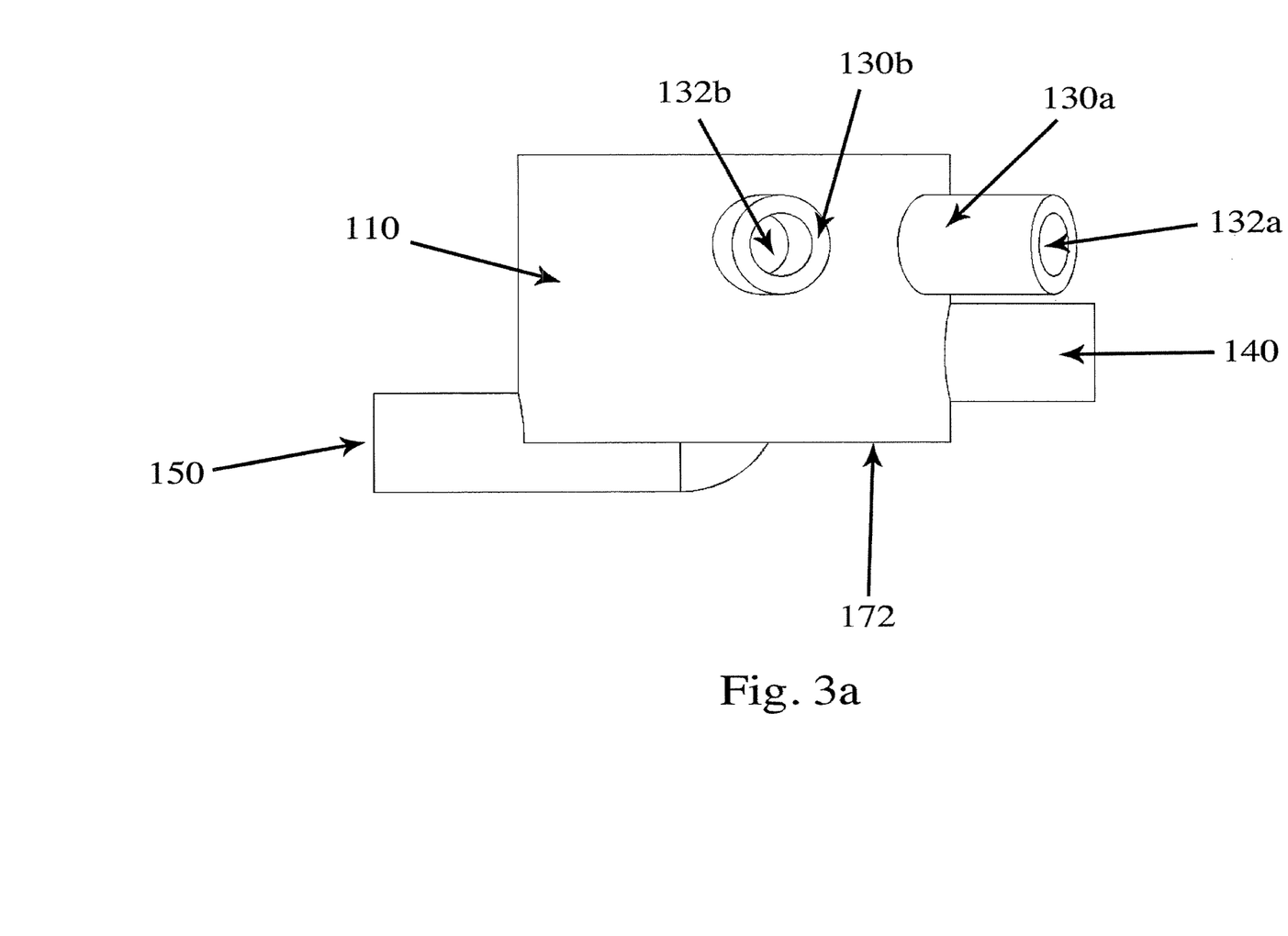
FIG. 3a is a side view of the cylindrical housing in FIG. 2.
Figure 3B:
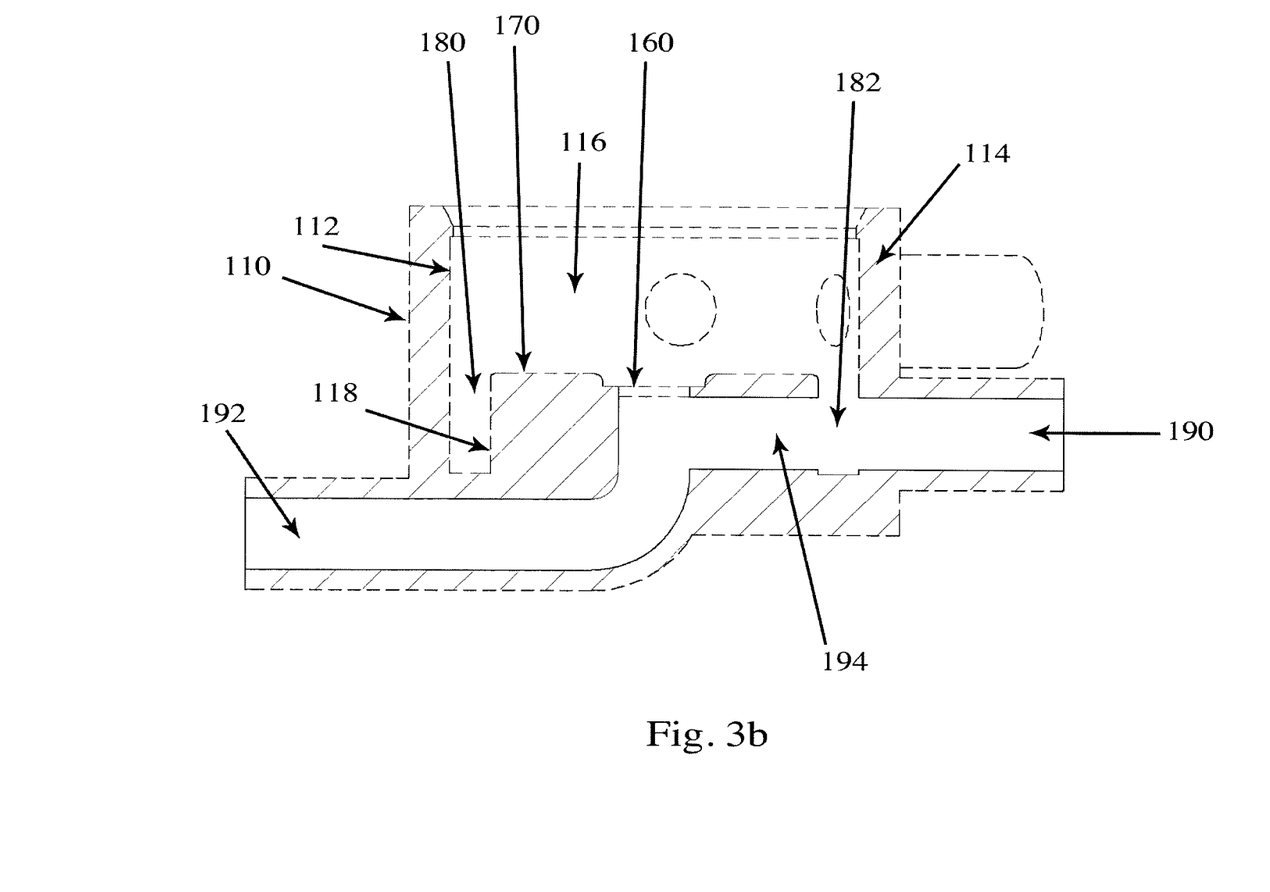
FIG. 3b is cross-sectional side view taken along the line B-B in FIG. 2.

Referring now to FIG. 2 and FIGS. 3a-b, the cylindrical housing 102 comprises a cylindrical housing wall 114 which encloses an inner cavity 116 into which the valve member is to be inserted. The cylindrical housing wall 114 comprises an outer envelope surface 110 and an inner cylindrical surface 112. Moreover, there is an annular seat 170 provided at the bottom of the cylindrical housing 102, outside of which there is a circular recess 180, 182 into which a projection of the valve member is to be fitted, see further below. In the center of the annular seat 170, there is provided a center hole 160. Furthermore, there is a groove 162 arranged around the hole 160 in the annular seat 170. Optionally, the annular seat 170 may be partly hollowed out in order to save the amount of material.

The cylindrical housing 102 further comprises in the shown embodiment four primary inlets 130a-d which are distributed circumferentially along the upper part of the outer envelope surface 110 in FIG. 1. The primary inlets 130a-d are integrally formed with the housing 102 and are shaped as pipes, or studs, which extend radially outwards from the outer envelope surface 110 of the housing 102. Thus, for each primary inlet 130a-d, there is an associated primary channel 132a-b which extends through each of the primary inlets 130a-d, and further through the housing wall 114, from the outer envelope surface 110 to the inner cylindrical surface 112. In the present embodiment, the center of each of the four primary inlets 130a-d is angularly separated by an angle of approximately 55° with respect to the center line of an adjacent primary inlet 130a-d.

According to the present embodiment, the primary inlets are distributed in the same axial plane. According to an alternative embodiment, however, the primary inlets may be distributed axially separated from each other.

Figure 4:
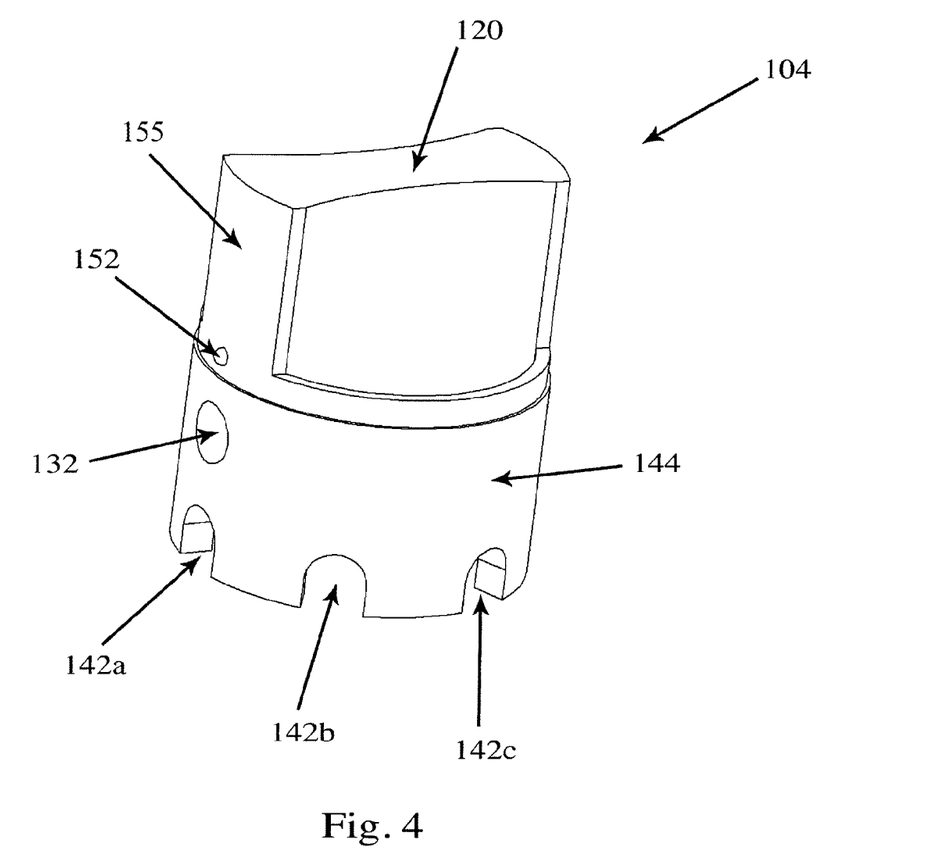
FIG. 4 is a perspective view of the valve member comprised in the valve shown in FIG. 1, as seen from the side.
Figure 5:
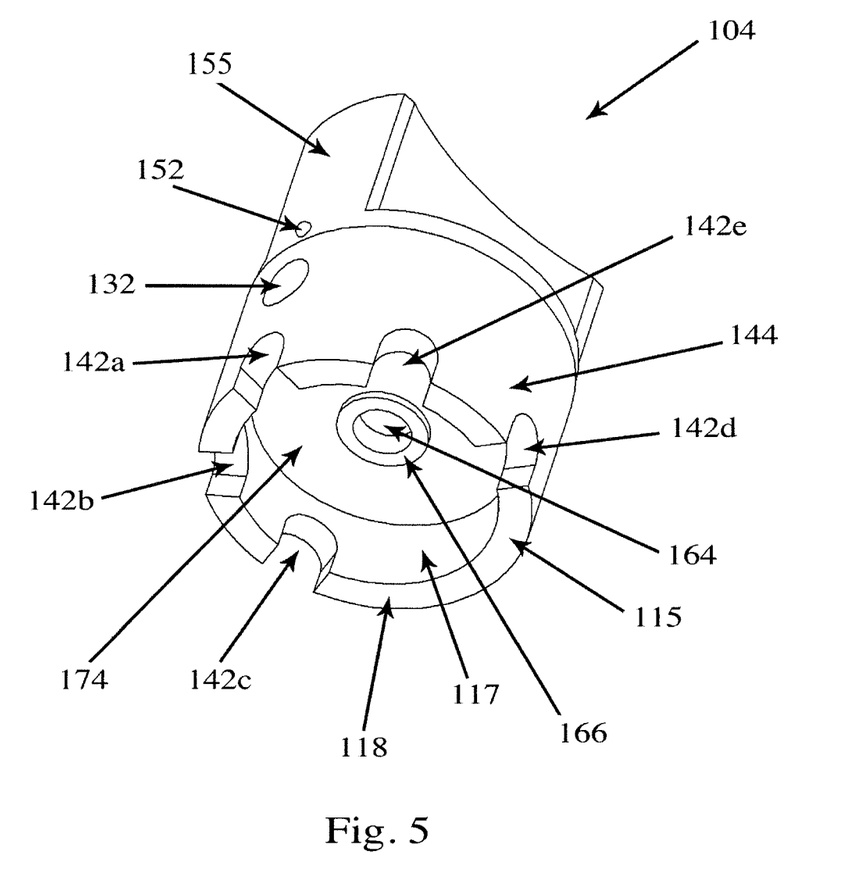
FIG. 5 is a perspective view of the valve member comprised in the valve shown in FIG. 1, as seen from the bottom.
Figure 6A:
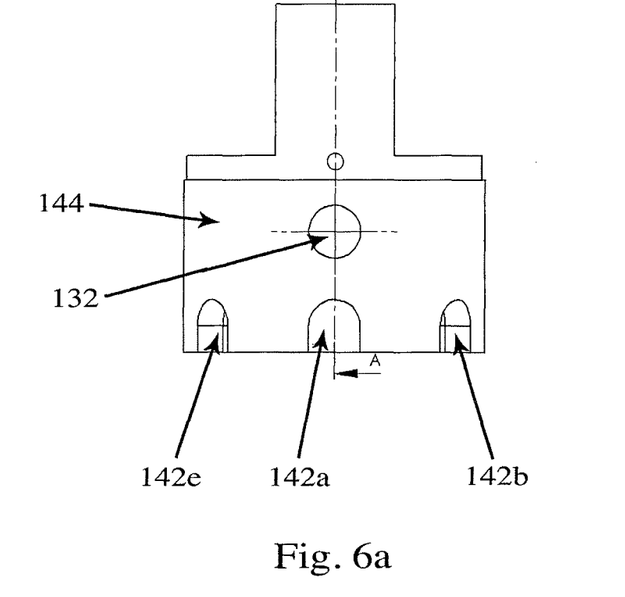
FIG. 6a is a side view of the valve member in FIG. 4.
Figure 6B:
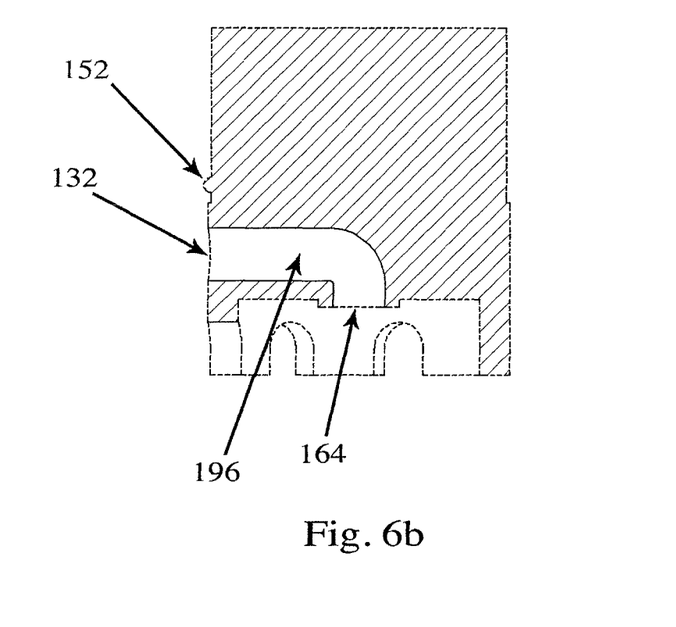

It is understood that any number of primary inlets may be provided on the outer envelope surface 110. Moreover, the angle between two adjacent primary inlets may be any angle between 0° and 180°. Preferably, however, the angle is such that two adjacent primary inlets do not overlap. More preferably, the angle is such that each first opening, comprised in a first set of openings, which is arranged in the outer cylindrical surface of the valve member (see FIG. 4), fits between any pair of adjacent primary inlets, at the inner cylindrical surface of the housing, so that fluid communication into the valve member may be prevented.

Moreover, the cylindrical housing 102 comprises a secondary inlet 140 which is arranged at the lower part of the outer envelope surface 110 in FIG. 1. In other words, the secondary inlet 140 is axially separated from the primary inlets 130a-d. The secondary inlet 140 is integrally formed with the housing 102 and is shaped as a pipe, or a stud, which extends radially outwards from the outer envelope surface 110 of the housing 102. Thus, there is an associated secondary channel 190 which extends through the secondary inlet 140 and further through the housing wall 114 from the outer envelope surface 110 to the inner cylindrical surface 112. Moreover, there is an intermediary channel 194 which extends from the side wall 118 of the annular seat 170 to the center hole 160. Thus, there may be fluid connection between the secondary inlet 140 and the center hole 160.

Moreover, as seen from the top, cf. FIG. 2, the secondary inlet 140 is angularly placed in between the adjacent primary inlets 130b and 130c. More specifically, the secondary inlet 140 is rotated approximately 27.5° clockwise with respect to the primary inlet 130c and approximately 27.5° counter-clockwise with respect to the primary inlet 130b.

The cylindrical housing 102 further comprises an outlet 150 which is integrally formed with the housing, and which is shaped as a pipe, or a stud. The outlet 150 extends radially outwards from the center of the back surface 172, and is rotated approximately 180° with respect to the second inlet 140, see e.g. FIG. 2. Thus, there is an associated outer channel 192 which extends from a hole in the outlet 150 to the center hole 160. Note that the channel 192 further is spatially connected to the secondary channel 190 via the intermediary channel 194 and the circular recess 182.

Referring to FIGS. 4-5 and FIG. 6a-b, the cylindrical valve member 104 is provided with a handle 120 by means of which the valve member 104 may be rotated. Moreover, the valve member 104 has a valve member wall 115 which has an outer cylindrical surface 144, an interior cylindrical surface 117, and a flat surface 174 in the center of which there is provided an aperture 164. The outer cylindrical surface 144 is provided with a first opening 132, and the interior cylindrical surface 117 is provided with five second openings 142a-e. The second openings are axially separated from the first opening. Of course, there may be any number of first openings provided in the outer cylindrical surface 144 and any number of second openings provided in the valve member wall 115. In the present embodiment, there is one more second opening 142a-e than there are primary inlets 130a-d.

Note that in the present embodiment, the secondary inlet 140 is angularly displaced with respect to two adjacent primary inlets 130a-d, being arranged half way between them with respect to the angular direction, while the first opening is angularly aligned with respect to one of the second openings. According to an alternative embodiment, however, the secondary inlet 140 may be angularly aligned with respect to one of the primary inlets 130a-d, while the first opening is angularly displaced with respect to two adjacent second openings. Preferably, the first opening is arranged half way between two adjacent second openings with respect to the angular direction.

It is also noted that if the primary inlets are arranged in the same axial plane, there is only need for a single first opening. The second openings 142a-e are formed in the shape of notches which are cut in the bottom 118 of the valve member wall 115. According to an alternative embodiment, the second openings 142a-e may be given by holes which are provided entirely within the valve member wall 115. From a manufacturing point of view, notches are preferred in comparison with holes in that they may be more easily designed by means of injection molding.

Moreover, there is an interior channel 196 extending from the first opening 132 to the aperture 164.

Optionally, in order to simplify the rotational operation of the valve member 104, there may be distinctive marks provided on the housing 102, such as colors, letters, arrows, symbols, etc.

Furthermore, there is a prominent circular part 166 arranged around the aperture 164. The prominent circular part 166 is adapted to tightly fit over the groove 162 which is arranged in the annular seat 170 of the housing 102.

Hence, referring back to FIG. 1, the valve member 104 may be joined with the housing 102. More specifically, the outer cylindrical surface 144 of the valve member 104 may sealingly engage, or equivalently tightly fit, the inner cylindrical surface 112 of the housing 102, such that the primary inlets 130a-d and the secondary 140 inlet are sealingly connected to the first opening 132 and the second openings 142a-e, respectively, which are arranged in the outer cylindrical surface. The valve member 104 may be rotated within the housing 102 into primary valve positions and intermediary valve positions. There may be additional valve positions, e.g. a closing position in which all fluid communication to the outlet is cut off.

By a primary valve position is meant a position at which an associated primary inlet 130a-d is connected to the outlet 150. According to the present embodiment, a primary valve position (labelled by e.g. $P_a$), is obtained when the valve member 104 is rotated to a position such that the first opening 132 faces a primary inlet (e.g. 130a). Thus, in this position, due to the tight fit there is fluid communication between the primary inlet 130a and the outlet 150 by means of the interior channel 196 and the outer channel 192 as described above. At the same time, fluid communications between the remaining primary inlets 130b-d, or the secondary inlet 140, and the outlet 150 are blocked. Thus, at a primary valve position (i.e. $P_a$), there is fluid communication between a primary inlet (i.e. 130a) and the outlet 150. According to the present embodiment, there may be four primary valve positions $P_a$, $P_b$, $P_c$, $P_d$.

Moreover, there are protrusions 152 arranged in the side parts 155 of the handle 120. These protrusions are arranged to engage with the recess 119 which is provided in the housing. By means of these protrusions 152, the valve member 104 may securely be rotated into the correct primary valve positions and be at least partially locked in these positions. In other words, a user of the valve 100 may be ensured that the valve member has been rotated to a correct position.

Optionally, there may be a check valve arranged in the channel 190 for the prevention of fluid escaping back into the secondary inlet 140.

By an intermediary valve position is meant a position in which the secondary inlet 140 is connected to the outlet 150. An intermediary position may be a position between two primary positions, spatially or temporally. According to the present embodiment, an intermediary valve position (labelled by e.g. $I_1$), is obtained when the valve member 104 is rotated to a position such that a second opening 142a-e faces the secondary inlet 140. Thus, due to the tight fit, in this position there is fluid communication between the secondary inlet 140 and the outlet 150 by means of the intermediate channel 194 and outer channel 192 as described above. At the same time, fluid communications between the primary inlets 130a-d and the outlet 150 are blocked. Thus, at an intermediary valve position (i.e. $I_1$), there is fluid communication between the secondary inlet (i.e. 140) and the outlet 150. According to the present embodiment, there are five possible intermediate valve positions $I_1, I_2, \ldots, I_5$.

There may be additional intermediary valve positions before the first primary position and after the last primary position. According to the present embodiment, there isone intermediary valve position before the first primary position and one intermediary valve position after the last primary position.

It is stressed that an intermediary valve position has to be passed when passing from one primary position to an adjacent primary position.

According to an alternative embodiment, the valve member may be lifted in an axial direction into the intermediary position. According to yet an alternative embodiment, the valve member may be pushed in an axial direction into the intermediary position.

The rotation of the valve member 104 may be manual, implemented by rotating the handle 120 by hand. Alternatively, the rotation of the valve member 104 may be automatic, in which case the handle 120 may e.g. be rotated by means of a machine. The rotations may be arranged to occur according to a predetermined schedule.

Optionally, there may be a closing position of the valve. In the closing position, all fluid communication between the primary inlets, as well as the secondary inlet, and the outlet are prevented. In one example, the valve member is rotated into the closing position within the housing. In another example, the valve member is put into the closing position by means of pushing, or alternatively pulling, the valve member in an axial direction. The closing position may be provided with a locking device.

Next, the valve 100 will be described in operation in a particular embodiment in the context of intravenous chemotherapy administration. Before utilization in medical applications, the valve 100 must be sanitized. Preferably, the disposable valve 100 is stored in a sterile bag before use.

In order to optimize the operation of the valve, the outlet 150 is preferably aligned with the direction of the gravitational field, i.e. the outlet 150 is preferably pointing downwards. Alternatively, however, the outlet 150 may be rotated with respect to the direction of the gravitational field, albeit with a suboptimal operation of the valve 100.

In the present embodiment, a first and a second drug solution, or equivalently drug fluid, comprising a first and a second type of cytostatics, are respectively led into two primary inlets, say 130a and 130b, by means of primary tubes, cf. the discussion above. Preferably, cut-off valves are provided on each of the primary tubes to allow for the flow of drug solution being cut off from the source. The source may e.g. be a bag storing the drug solution. The type of drug solutions as well as their dosages depend on the type of cancer, the stage of the cancer, the type of chemotherapy, the characteristics of the patient, etc. The dosage of the fluids may be varied e.g. by controlling the flow of the fluids. The primary inlets 130a and 130b are provided with drug connection devices for connecting the drug-carrying tubes. In a non-limiting example, drug connection devices comprises male and female Luer connectors. The Luer connectors may be molded together with the housing, or alternatively, be arranged on a premolded housing. It is clear, however, that any type of drug connection devices may be used. In the present embodiment, the connection devices are provided with check valves in order prevent back flow of fluids. To prevent fluids from escaping from the valve through the remaining two primary inlets 130c and 130d, these are sealed by means of plugs. Alternatively, the primary inlets 130c and 130d may be provided with check valves in order to accomplish the same effect. Optionally, there is provided a check valve in the interior channel 196.

To clearly separate the primary inlets from each other, they may be provided with different characteristics, such as colors, letters, numbers, symbols, etc. For example, the characteristics of a primary inlet may coincide with a corresponding characteristics of the bag in which the drug solution to be fed into the primary inlet is stored.

Moreover, a neutral fluid, such as a saline solution, or equivalently a saline fluid, is led into the secondary inlet 140 by means of a tube as described in the above. The saline solution may comprise a sterile solution of sodium chloride (NaCl). The secondary inlet 140 is provided with a saline connection device for connecting the saline-carrying tube. In a non-limiting example, saline connection devices comprises male and female Luer connectors. It clear, however, that any type of saline connection devices may be used. The saline connection device does not comprise any check valve. Preferably, the saline solution is led into the valve by means of the gravitational force. Moreover, cut-off valves are preferably provided on the saline-carrying tube to allow for the flow of saline solution being cut off from the source, which may be a bag storing the saline solution.

Preferably, cut-off valves are provided on the saline-carrying tube to allow for the flow of saline solution being cut off from the source. The source may e.g. be a bag storing the saline solution.

According to an alternative embodiment, a check valve provided in the intermediary channel 194 may replace all of the check valves which are provided in the primary inlets.

Initially, the valve member is rotated into a first intermediate position, $I_1$, which is provided before the primary position of the first drug solution in the given rotational direction, say the clockwise direction. In the first intermediate position, saline solution is led from the secondary inlet 140 to the outlet 150 as described in detail above.

Next, the valve member is rotated into the primary position $P_a$ of the first drug solution. In this primary position, the first drug solution is led from the primary inlet 130a to the outlet 150 as described in detail above.

Thereafter, the valve member is rotated into a second intermediate position, $I_2$, which is provided between the primary position of the first drug solution and the primary position of the second drug solution. As in the first intermediate position, saline solution is led from the secondary inlet 140 to the outlet 150 also in the second intermediate position.

It is noted that in the transition between the first drug solution and the saline solution, these fluids may temporarily mix. Indeed, one purpose of having the saline solution, is to remove residuals of the drug solution from the outer channel 192 and the interior channel 196 as well as their surroundings, and from the catheter tube which is connected to the patient. Another purpose of having the saline solution, is to create a fluid buffer between the first and second type of drug solutions which separates them from each other. The mixing of the first drug solution and the saline solution in the channel 196 is negligable, since this channel is substantially pointing downwards in operation, thereby efficiently leading the fluids away.

In an alternative embodiment, the interior channel 196 is not shaped as a channel which is curved 90° as in the present embodiment, but rather has a substantially straight form pointing downwards. This embodiment may further reduce the amount of mixing of fluids in the interior channel 196 by increasing the flow of the fluids due to the gravitational field.

The valve member is then rotated into the primary position $P_b$ of the second drug solution. In this primary position, the second drug solution is led from the primary inlet 130b to the outlet 150 as described in detail above.

Lastly, the valve member is rotated into a third intermediate position, $I_3$, which is provided after the primary position of the second drug solution in the given rotational direction. As in the first intermediate position, saline solution is led from the secondary inlet 140 to the outlet 150 also in the third intermediate position.

Thus, it is emphasized that there is no way of passing from one primary position to another primary position without passing an intermediary position. As a consequence, there is no way of mixing two drug solutions.

Thus, the rotational sequence of the valve member according to the present embodiment may be summarized by the valve positions: $(I_1, P_a, I_2, P_b, I_3)$.

According to an alternative embodiment, the valve member may be rotated only in a specific angular direction, say the clockwise direction. The fixation to the specific orientation may be implemented e.g. by means of a tap.

However, the order in which the above steps have been carried out are not fixed by the embodiment given above. For example, if it is noted, when flushing with saline, that there is some remaining drug solution in the bag of a previously inserted drug solution, one may rotate the valve member back to the corresponding primary position in order to empty the bag.

A typical saline infusion into a patient comprises 50 ml saline solution before the first drug solution is inserted, 15 ml saline solution between a first and a second drug solution, and 100 ml saline solution after the last drug solution has been inserted. A typical lifetime of the valve ranges from 12 hours to 72 hours, but also other lifetimes are conceivable.

Hence, by alternately feeding saline solution and drug solutions into the bloodstream of the patient, there is a constant escape of fluid from the valve. Thereby, the risk of passing gas bubbles, such as air bubbles, into the patient is reduced.

In addition, by means of the inventive valve, the risk of supplying the fluids in the wrong order to the patient is reduced. Also, due to the construction of the valve, in which only one type of drug fluid may escape from the outlet, there is no risk of supplying two different drug solutions simultaneously to the patient. Note, however, that in a valve-member position situated between a primary position and an intermediary position, there may be mixing of a drug solution and the saline solution, i.e. a drug solution and the saline solution may come out from the outlet simultaneously.

By means of the intermediary positions, the risk of mixing two different drug solutions in the catheter tube which is passed on to the patient is greatly reduced. The intermediary position is a position temporally, and optionally also spatially, between two primary positions.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. Valve for administration of a plurality of drug fluids, comprising:
   a. a rotational axis;
   b. a housing having:
      an inner housing cavity presenting a cylindrical or frustoconical inner sealing surface extending circumferentially in relation to the rotational axis;
      a plurality of primary inlets circumferentially spaced in relation to each other about the rotational axis and arranged to receive a respective one of said drug fluids; and
      a secondary inlet arranged to receive a secondary fluid;
   c. a single outlet having an exit and an entrance, the entrance of the outlet being centrally located within the housing coaxially with the rotational axis;
   d. a valve member being arranged in the inner housing cavity for rotation about the rotational axis, said valve member having:
      a cylindrical or frustoconical outer sealing surface extending circumferentially about the rotational axis, said inner and outer sealing surfaces being in sealing engagement with each other;
      a primary opening arranged in the outer sealing surface at a first axial level of the valve; and
      a set of secondary openings arranged in the outer sealing surface at a second axial level, wherein said first and second axial levels are axially spaced from each other with respect to the rotational axis;
   e. wherein the valve member being arranged, by rotational movement only about the rotational axis, to be positioned into a plurality of primary valve positions and a plurality of intermediary valve positions different from the primary valve positions, said primary and intermediary valve positions being circumferentially spaced in relation to each other about the rotational axis such that an intermediary valve position has to be passed when rotating the valve member from one primary valve position to an adjacent primary valve position;
   f. wherein, in each selected primary valve position, an associated one of the primary inlets, associated with the selected primary valve position only, is connected to the primary opening and from the primary opening connected to the centrally located entrance of the outlet; and
   wherein, in each selected intermediary valve position, the secondary inlet is connected to an associated one of the secondary openings, associated with the selected intermediary valve position only, and from said associated one of the secondary openings connected to the centrally located entrance of the outlet.

2. Valve according to claim 1, wherein the inner circumferential surface of the housing is a cylindrical inner surface, and the outer circumferential surface of the valve member is a cylindrical outer surface.

3. Valve according to claim 2, wherein the primary inlets are integrally formed with said housing.

4. Valve according to claim 2, wherein the secondary fluid is a neutral fluid.

5. Valve according to claim 1, wherein the set of secondary openings of the valve member comprises at least a number of secondary openings corresponding to the number of primary inlets.

6. Valve according to claim 5, wherein the set of secondary openings of the valve member comprises a number of secondary openings corresponding to the number of primary inlets plus one.

7. Valve according to claim 1, wherein the primary inlets are integrally formed with said housing.

8. Valve according to claim 1, wherein the secondary fluid is a neutral fluid.

\* \* \* \* \*